(12) United States Patent
Day et al.

(10) Patent No.: US 10,169,534 B2
(45) Date of Patent: Jan. 1, 2019

(54) MEDICAL IMAGE DISPLAY SYSTEM AND METHOD

(71) Applicant: Toshiba Medical Systems Corporation, Otawara-shi (JP)

(72) Inventors: Timothy Day, Edinburgh (GB); Dominic Ashmole, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/041,291

(22) Filed: Sep. 30, 2013

(65) Prior Publication Data

US 2015/0091778 A1    Apr. 2, 2015

(51) Int. Cl.

| G06F 19/00 | (2018.01) |
| G06F 3/14 | (2006.01) |
| G06T 19/00 | (2011.01) |
| G16H 40/63 | (2018.01) |
| A61B 5/00 | (2006.01) |

(52) U.S. Cl.
CPC .......... *G06F 19/321* (2013.01); *G06F 3/1446* (2013.01); *G06F 3/1454* (2013.01); *G06F 19/00* (2013.01); *G06T 19/00* (2013.01); *G16H 40/63* (2018.01); *A61B 5/6898* (2013.01); *A61B 5/7425* (2013.01); *G06T 2210/41* (2013.01); *G09G 2340/0492* (2013.01); *G09G 2370/042* (2013.01); *G09G 2380/08* (2013.01)

(58) Field of Classification Search
None
See application file for complete search history.

(56) References Cited

U.S. PATENT DOCUMENTS

| 8,571,289 | B2* | 10/2013 | Ruth et al. .................... 382/131 |
| 2004/0263424 | A1 | 12/2004 | Okuley |
| 2005/0249239 | A1* | 11/2005 | Pierce ................. G06F 19/3418 370/466 |
| 2007/0076245 | A1 | 4/2007 | Sugimoto et al. |
| 2008/0146277 | A1* | 6/2008 | Anglin et al. ............. 455/556.1 |
| 2008/0240524 | A1 | 10/2008 | Kariathungal et al. |

(Continued)

FOREIGN PATENT DOCUMENTS

| DE | 10 2008 059 456 B3 | 8/2010 |
| JP | 05-269119 | 10/1993 |

(Continued)

OTHER PUBLICATIONS

"Digital Imaging and Communications in Medicine (DICOM)", Supplement 60: Hanging Protocols, DICOM Standards Committee, Working Group 11, Display, Jan. 18, 2005, 108 pages.

(Continued)

*Primary Examiner* — Duane N Taylor, Jr.
(74) *Attorney, Agent, or Firm* — Oblon, McClelland, Maier & Neustadt, L.L.P.

(57) ABSTRACT

A display system for displaying medical images across a plurality of separate display devices, the system comprising a layout unit for providing layout data concerning the display of medical images, an allocation unit for allocating a plurality of medical images amongst a plurality of separate display devices according to the layout data, wherein at least one of the plurality of display devices comprises a mobile display device.

32 Claims, 7 Drawing Sheets

(56) References Cited

U.S. PATENT DOCUMENTS

| | | | |
|---|---|---|---|
| 2009/0160731 A1* | 6/2009 | Schuler | G06F 3/1423 345/1.1 |
| 2009/0164253 A1* | 6/2009 | Lyshkow | 705/3 |
| 2009/0184849 A1* | 7/2009 | Nasiri et al. | 341/20 |
| 2009/0237560 A1* | 9/2009 | Ganzaroli | H04N 5/04 348/511 |
| 2009/0243957 A1 | 10/2009 | Ni et al. | |
| 2013/0335408 A1* | 12/2013 | Yi et al. | 345/419 |

FOREIGN PATENT DOCUMENTS

| | | |
|---|---|---|
| JP | 2003-289475 | 10/2003 |
| JP | 2005-276200 | 10/2005 |
| JP | 2006-195675 | 7/2006 |
| JP | 2010-155104 A | 7/2010 |
| JP | 2013-156371 A | 8/2013 |
| WO | WO 2005/093593 A1 | 10/2005 |

OTHER PUBLICATIONS

Combined Office Action and Search Report dated Jul. 14, 2016 in Chinese Patent Application No. 201410513144.7 (with English translation of Categories of Cited Documents).

Office Action dated May 8, 2018, in the corresponding Japanese Patent Application No. 2014-171963; citing documents AO and AP therein. 57 pages.

* cited by examiner

MEDICAL IMAGE DISPLAY SYSTEM AND METHOD

FIELD

Embodiments described herein relate generally to systems, user interfaces, devices and methods for displaying medical images and data.

BACKGROUND

Prior to the advent of digital medical imaging, images were film-based and would be attached or "hung" on vertical light-boxes for review by clinicians such as radiologists. Typically, support staff would prepare the case for reading, hanging the images according to a chosen hanging protocol. The hanging protocol would define the relative hanging positions of the images according to criteria such as date/time of acquisition, orientation of acquisition, anatomy, type of study, preference of the reading clinician.

Modern medical imaging devices such as CT scanners or MRI scanners can provide a variety of different views of a region of interest. Increasingly, medical images are reviewed in digital format on high-resolution computer monitors. One method of review is using viewing software supplied with a Picture Archiving and Communications System (PACS) or associated with scanner devices. This software divides the display into a number of views, for example rectangular areas each of which displays an image or associated information. Such views can comprise, for example, views in different planes such as coronal, sagittal and axial planes and/or different types of views such as 2D sectional views, 3D or pseudo 3D rendered views and the like.

Display of images using software allows for more flexible methods of display, and radiologists have adapted their review methods to take advantage of these new capabilities. A basic example is the ability to scroll through a set of related images within a single view rather than displaying them simultaneously in many separate views. An extension of this is to spatially and/or temporally register multiple sets of images and scroll through them in synchrony. A further extension is to display additional localizer images, for example images acquired orthogonally to the primary images, and display cross-section indicator lines on these, indicating the anatomical location of the primary images.

PACS viewers or similar other viewers offer a wide range of additional capabilities, including contrast adjustment, measurement, panning, zooming, and so on, some of which may optionally be applied to multiple linked views simultaneously. In general, a characteristic of such viewers is that the user interacts with the views using, for example a mouse, a touch screen or a keyboard, and the images in the view, and in related views, change accordingly.

A PACS or other software-based hanging protocol, rather than being a set of encoded preferences/instructions enacted by support staff on receipt of film-based images, may be a software-automated display method either automatically applied based on some matching rules, or selected from a list by a user, when loading digital images. The Digital Imaging and Communications in Medicine (DICOM) standard provides optional guidance for the construction and interpretation of such hanging protocols.

When analysing such imaging data, it is often beneficial to view a region of interest using a variety of concurrently displayed views of the region, e.g. using a multiplanar reconstruction (MPR), or to present a selection of associated views of the same or different regions. For example, this may allow views in different planes or different image types to be presented simultaneously for direct comparison.

The selection of the views for display and the order and relative positioning of the views can be specified by a hanging protocol. The use of hanging protocols ensures that the views are presented to the user in a consistent and repeatable manner and in a way that allows for optimal analysis. For instance, in a simple example a hanging protocol for analyzing for a particular condition associated with a particular body part may specify a 2×2 grid, with a transverse or axial view in the top left hand corner, a view in the coronal plane in the top right hand corner and a sagittal view in the bottom left hand corner.

For more specialist tasks, various forms of advanced visualization may be performed. For example, Multi-Planar Reformatting (MPR) processes the original images produced by a CT, MRI or other three-dimensional scanner to produce cross-sectional images at any other orientation through the patient. Various forms of 3D volume rendering process the original images to provide near-photo-realistic 3D representations of anatomy. Automatic segmentation techniques identify and highlight or hide particular anatomical structures. Many other similar advanced techniques and rendering modes exist.

Advanced visualization techniques greatly expand the type of views and the potential interactions and linkages between them. For example, on loading images of a portion of the vasculature, software may provide MPR views in Axial, Coronal and Sagittal planes, a 3D Shaded Volume View, a Curved Planar Reformatting view derived from a manually or automatically determined vessel centreline, and one or more planar MPR views orthogonal to particular points on the vessel centreline. Changing the contrast in one MPR view may similarly change the contrast on some or all of the other MPRs. Scrolling, panning or zooming one MPR view may cause related changes to other MPRs. Editing a vessel centreline may be performed on one or more views, causing updates to other views. Additionally, some of these views may be judged to be of lower diagnostic importance or relevance than others.

Choosing which views to include, how the views interact, and the relative sizes and positions of views is part of the skill of product design for advanced visualization software. These choices can also be regarded, or offered, as types of hanging protocol.

The main work of a radiologist may be done within a darkened radiology reading room, using one or more specialist high-resolution monitors connected to a computer workstation and/or server. However, other types of users exist, for example surgeons, oncologists, cardiologists, nurses and so on. These users may view medical images on separate specialist systems, designed, for example, for the surgical theatre or for carrying between hospital wards. Alternatively, they may use systems providing easy access to images from a standard desktop or laptop computer, or mobile tablet device, perhaps through software hosted within a web browser. Similarly, radiologists working on call from home may use teleradiology viewers providing image review functions requiring less screen space and network bandwidth. From the above, it can be appreciated that hanging protocols may vary according to individual preference, user role, available hardware, location, context, and so on.

It is common for radiologists and other types of user to collaborate face-to-face while reviewing or discussing images and associated data. For example, it is common practice to discuss treatment decisions in multi-disciplinary team meetings or other, less formal interactions.

In the case of a collaboration between, say, a radiologist and a surgeon, the radiologist may, for example, be using a laptop and the surgeon may have a tablet device. Each of the users must separately look up and load the relevant patient data from some source (local hard disk or over a network via wireless or cable). Each user may have different, role-specific viewing software. They may be unused to each other's viewing software and this may hinder easy interpretation of the case. Each viewing software may behave entirely independently of the other. There is no linkage of navigation, visualization settings and so on.

Because one or both of the radiologist and the surgeon are away from their typical viewing environment (which may include multiple specialised displays) their standard hanging protocol may be unsuited to the display they have brought with them to the collaboration. For example, there may be insufficient space for both the essential views and the less essential ones. The shape and resolution of the display may fail to match the requirements of the standard hanging protocol (e.g. convenient full size display of two 512×512 pixel images)

FIG. 1 shows an implementation of a hanging protocol in a multiplanar reconstruction (MPR) image display system 5. This image display system 5 comprises a workstation 10 having a processing unit 15 and an associated display unit 20. The display unit 20 comprises, for example, a high resolution 10 Mpixel display. Upon initiating a work session, the purpose of the session is established, e.g. the modality used and the procedure that it is being used in connection with. The relevant properties of the attached display unit 20, such as the resolution and size of the display are also established.

Each hanging protocol may have an associated set of rules that set out the circumstances in which the hanging protocol is applicable, for example the purposes and display properties it can be used for. In this way, a hanging protocol appropriate for the session can then be selected. The processing unit 15 then configures the display unit 20 to display the required images in the relative positions specified in the hanging protocol.

Each of the views should be displayed with an acceptable resolution and size in order to allow the user to identify and assess the relevant image features. In order to provide acceptable views, many image display systems use very high resolution display technology, such as 10 Mpixel monitors. It will be appreciated that the high resolution display units 20 favoured in systems such as that of FIG. 1 can be expensive and such systems tend to be bulky, heavy and lack portability.

Devices such as workstations, tablet computers, smartphones and the like are becoming increasingly common in hospitals. However, the display units used by these devices are generally of significantly lower resolution than the high resolution displays used by medical image display systems such as that of FIG. 1. For example, the screen of an Apple® iPhone® 4s is 906 pixels by 640 pixels at a resolution of 326 pixels per inch, whilst an Apple® iPad® 2 has a 1024 pixel by 768 pixel screen at a resolution of 132 pixels per inch. It will be appreciated that these specifications are significantly below the specifications of displays commonly found in modern specialist medical image display systems.

Despite advances in monitor technology, alternative ways of displaying of medical imaging data may be desirable.

BRIEF DESCRIPTION OF THE DRAWINGS

Embodiments are now described, by way of non-limiting example, and are illustrated in the following figures, in which.

DETAILED DESCRIPTION

Figure 1:
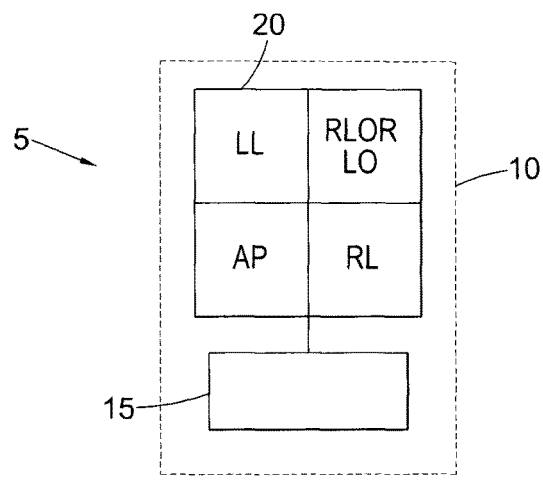
FIG. 1 shows an example of use of a hanging protocol in a medical imaging system.

Certain embodiments provide a display system for displaying medical images across a plurality of separate display devices, the system comprising a layout unit for providing layout data concerning the display of medical images, and an allocation unit for allocating a plurality of medical images amongst a plurality of separate display devices according to the layout data, wherein at least one of the plurality of display devices comprises a mobile display device.

Certain embodiments also provide a mobile display device for displaying medical images in collaboration with at least one other display device, the mobile display device comprising a display, a communication unit for communicating with the at least one other display device, a layout unit for providing layout data concerning the display of medical images, and an allocation unit for allocating a plurality of medical images to the display device and at least one other display device according to the layout data.

Certain embodiments also provide a method for displaying medical images across a plurality of separate display devices, the method comprising providing layout data concerning the display of medical images, and allocating a plurality of medical images amongst a plurality of separate display devices according to the layout data, wherein at least one of the plurality of display devices comprises a mobile display device.

A medical image display system according to an embodiment provides a system 105 for facilitating, initiating and configuring use of a plurality of display devices 110*a-d*, which may be mobile display devices, to co-operatively display medical images.

Images 112*a-d* are allocated by the system to specific display devices 110*a-d* from a plurality of display devices according to layout data that, in this case comprises a hanging protocol.

The layout data can comprise a plurality of rules concerning, for example, at least one of allocation to a display device, image appearance, image orientation, image data selection, image rendering, image importance, image navigation.

The image display system 105 is configured to collect position and/or relative position and/or proximity data that indicates or is usable to determine the relative positions and/or proximity of the display devices 110*a-d*. The hanging protocol specifies a plurality of images 112*a-d* to be displayed and the relative positions of the images 112*a-d* to be displayed. The image display system 105 is configured to allocate each of the images 112*a-d* to be displayed to a display device 110*a-d* whose position and/or relative position best reflects the position and/or relative position for the allocated image 112*a-d* specified in the hanging protocol.

In this way, a feature specific to medical image display systems, a hanging protocol, can be used to easily and optionally automatically configure multiple displays to operate as a combined display for displaying multiple medical images in a medical image display system.

Figure 2:
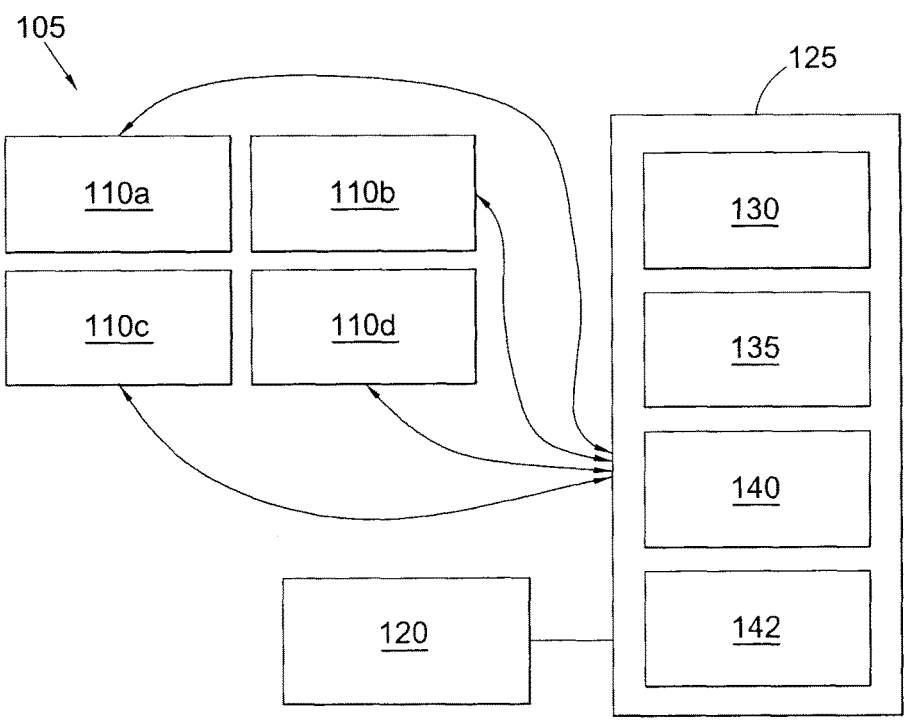
FIG. 2 is a schematic diagram of an image display system according to an embodiment of the invention.

A medical image display system 105 according to a first aspect is schematically illustrated in FIG. 2. The medical image display system 105 is operable, for example, as a multiplanar reconstruction (MPR) image display system. The image display system 105 comprises a plurality of display devices 110*a-d*, data storage 120 and processing apparatus 125 in the form, in this case, of a server. As will be explained below, the display devices 110*a-d* can be selected to join the image display system 105 by a user action or can be automatically detected and joined.

The various functions of the image display system 105 can be distributed in a variety of ways in different embodiments. For example, in the embodiment of FIG. 2, the image display system 105 comprises or is comprised in a server/client based system, wherein the images 112*a-d* or image data for generating the images, and/or the processing apparatus 125 are provided remotely to the display devices 110*a-d*.

In the embodiment of FIG. 2, data storage 120 stores image data and is linked to the server 125, which is configured to communicate remotely with the display devices 110*a-d*, which operate as thin clients. In this case, the display devices 110*a-d* can communicate with the server(s) to provide user input, user data, device data and any other data stored or input to the display device 110*a-d* and the appropriate images 112*a-d* for display are rendered by the server 125 and provided to the appropriate display devices 110*a-d* by the server(s) along with instructions to display the images, based on the hanging protocol. In some alternative embodiments, the server 125 instructs the display devices 112*a-d* concerning the images to be displayed on each display device 112*a-d* but rendering (for example rendering of 2D representations of 3D image data) is performed locally at the display devices 112*a-d* themselves to generate the images for display.

In alternative embodiments, one of the display devices 110*a-d* is configured to perform the function of the server 125 and/or data storage 120, or two or more of the display devices 110*a-d* co-operate together to provide the function of the server 125 and/or the data storage 120. Thus, the processing functions of the server 125 may be distributed across one or more of the display devices and no additional server may be required.

Figure 3:
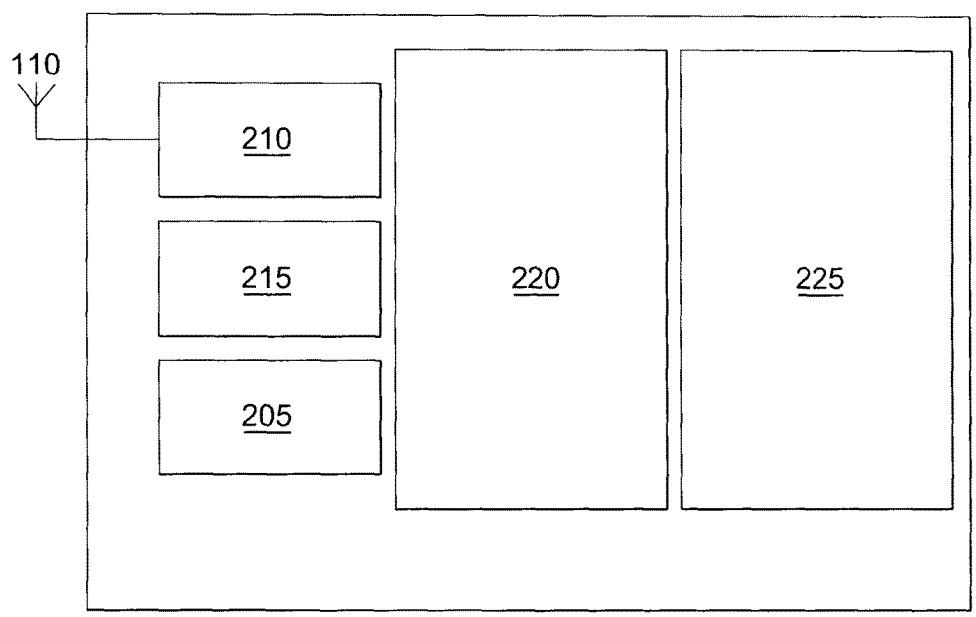
FIG. 3 is a schematic diagram of a display device for use with the system of FIG. 2.

A suitable display device 110 for use with the image display system 105 is shown in FIG. 3. Examples of suitable display devices 110 include computer workstations, laptops, tablet computers, smartphones, networkable televisions and monitors, and the like. At least some of the display devices 110 may be portable.

Each display device 110 comprises device data storage 205, a communications unit 210, a display 220, and optionally a position determining apparatus 215, which in this case incorporates a device discovery unit configured to discover display devices in a vicinity of the device 110.

The display device data storage 205 is configured to store data such as data identifying the display device 110, data indicating the type of display device 110, data indicating properties of the display such as resolution and size and user data relating to a user associated with the display device 110 such as job title, expertise, name, interests, preferences and the like. However, it will be appreciated that some or all of the above data need not be stored in the data storage 205 and may instead be stored in external data storage 120 and/or accessed over a network.

The communications unit 210 is configured to communicate with the communications units 210 of other display devices 110 and/or the server(s) and/or remote data storage 120. The display device communications unit 210 can comprise suitable wired or wireless communications apparatus.

The device discovery unit of the position determination apparatus 215 is configured to discover display devices in a vicinity of the display device. The position determination apparatus 215 is also configured to collect or determine positional data that indicates or is usable to determine the position and/or relative positions of one or more of the display devices 110*a-d*. The position determination apparatus 215 or device discovery unit may comprise one or more of satellite position apparatus such as GPS or Galileo positioning apparatus, near field communications apparatus, RFID apparatus, Bluetooth, zigbee or other short range communications apparatus, accelerometers, cameras, and the like.

In some embodiments, the position determination apparatus 215 comprises a GPS sensor that is operable to determine a position of the display device(s) 110*a-d*. The GPS data from several display devices 110*a-d* can be shared or provided to a server such that it can be used to identify other display devices 110*a-d* in proximity.

In other embodiments, the position determination apparatus 215 comprises a camera mounted on at least two and optionally each display device 110*a-d*. Images from the cameras can be analysed to determine and compare overlaps in the images collected by differing display devices 110*a-d*. The overlaps can be used to determine the relative position and orientation of adjacent or nearby display devices 110*a-d*.

In a further example, the position determination apparatus 215 comprises an accelerometer or other sensor, which may be operable to determine gestures intended to indicate that another display device 110*a-d* is present and its relative position. For example, accelerometers within a display device 110*a-d* can be used to determine a "bumping" action, wherein the determination of the "bumping" action signifies the presence of another display device 110*a-d* and the direction of the "bumping" action is indicative of the relative position of the other display device 110*a-d*.

In some embodiments devices that contain accelerometers, or other devices that can be used to determine orientation, are configured to re-orient displayed images automatically in response to reorientation of the device. Thus, the orientation of displayed medical images can be updated automatically in response to a change of orientation of the display device.

In another example, the position determination apparatus 215 comprises a wireless transmitter/receiver arrangement, such as near field communications apparatus, wherein signals transmitted by a display device 110a-d can be received and analysed by other display devices 110a-d in order to detect and identify proximate display devices 110a-d. Optionally, the direction of the signal can be identified, e.g. by a directional receiver, in order to also identify the relative position of the other display device(s) 110a-d.

In addition, although the display devices 110 are advantageously provided with at least one automated position determination apparatus 215, such as those listed above, this need not necessarily be the case. For example, alternatively or additionally to the above, a user could simply input at least a display device identifier and manually input the relative position of the display device 110, for example by using a key or text input or by performing a gesture such as a touch screen gesture.

The position determination apparatus 215 is not limited to those described above and other position determination apparatus 215 and techniques that can be used to identify and/or determine the position and/or relative position of display devices 110a-d would be apparent to a skilled person.

The system data storage 120 is configured to store the images 112a-d and/or image data used to produce the images, and data used by the image display system 105 such as the hanging protocols, user preferences and other user data and/or device data such as display sizes, display resolutions, and/or the like. In alternative embodiments, the data storage may comprise data storage on one or more display devices and/or networked data storage as well as or instead of comprising a separate data storage 120 associated with a server 125.

The server 125 in the embodiment of FIG. 2 comprises or implements at least one position determination unit 130 for providing the relative positions of the display devices 110a-d, a layout unit 135 for providing a hanging protocol for displaying the images; an allocation unit 140 for allocating the images to selected display devices 110a-d based on the hanging protocol and the relative position of the display devices 110a-d; and a display and rendering unit 142 for rendering images from stored image data for distribution, and for instructing the display devices 110a-d to display the images.

The position determination unit 130 determines the relative positions and/or proximities of each of the display devices 110a-d, for example, based on position and/or relative position data received from the display devices 110a-d.

The layout unit 135 is configured to select an appropriate hanging protocol for the display session. The hanging protocol specifies the images 112a-d to be displayed such as images of particular planes (e.g. sagittal, coronal, transverse, axial, etc.) and/or type (e.g. 2D, 3D rendered, etc.), along with the relative position in which each image 112a-d is to be displayed. Hanging protocols may be specified using the DICOM standard (Digital Imaging and Communications in Medicine (DICOM) Supplement 60: Hanging Protocols, DICOM Standards Committee, Working Group 11 Display, 1300 N. 17th Street, Suite 1847, Rosslyn, Va. 22209 USA, 18 Jan. 2005). The hanging protocols are not limited to standard protocols and could instead comprise user customized or generated hanging protocols, for example.

The layout unit 135 is configured to collect any data that it needs to select a suitable hanging protocol. For example, this could comprise session data, user data and/or device data. The session data comprises data such as a purpose of the session, modality, the body part being imaged, the procedure that the imaging is part of, and/or the like. The user data comprises data such as a user's role, title, experience, interests, clearance, permissions, personal preferences and/or the like. The device data comprises data such as display size, display resolution, display capabilities, model type, and/or the like, for one or more display devices. The data collected by the layout unit 135 can be input by a user and/or retrieved from device 110a-d based data storage 205 and/or networked storage, as appropriate.

The layout unit 135 is configured to select an appropriate hanging protocol from those stored on the data storage 125, or that are otherwise accessible, that best matches the data collected by the layout unit 135. For example, each hanging protocol is supplied with a set of rules outlining the conditions under which the hanging protocol can be used. In this case, the layout unit 135 can be configured to compare the data it has collected with the rules specified in the hanging protocols in order to identify a best match and thereby determine the most suitable layout protocol. Alternatively or additionally, the most appropriate layout protocol can be selected by manual user selection.

The allocation unit 140 is configured to identify a display device 110a-d having a position relative to the other display devices 110a-d (as determined by the position determination unit) that best matches or corresponds with one or more relative image positions specified in the selected hanging protocol. The allocation unit 140 is configured to allocate at least one image 112 to the display device 110a-d having a location relative to the other display device(s) 110a-d that best matches or corresponds with the relative image position specified in the hanging protocol for the allocated image 112.

In an alternative mode of operation, the position determination unit 130 determines the relative proximities of the display devices in an area and selects those display devices that are separated by less than a threshold distance of one another. The hanging protocol is then used by the allocation unit 140 to allocate images to different ones of the display devices that are separated by less than the threshold distance. In a variant of that embodiment, a list of the available devices that are within a threshold distance is displayed to a user via one or more of the display devices. The user is able to provide input to select devices from the list with which to collaborate, and the allocation unit 140 then allocates the images between the selected devices in accordance with the hanging protocol, subject to consent from the selected devices. The list may be a list of devices that are within the threshold distance of the display device of the user.

It will be appreciated that the images 112 can be provided from any suitable source such as from the system data storage 120, data storage 205 on one or more of the display devices 110a-d, data obtained directly from one or more associated or connected medical imaging devices (not shown) or from data accessed remotely by any other means, such as over a network, for example. Images may be retrieved, for example, from a picture archiving and communication system (PACS) is particularly preferable.

The image display system 105 described above uses the plurality of display devices 110a-d to form a combined display, wherein the image display system 105 operates using hanging protocols to specify the types of images 112 to be displayed and their relative positions and then allocates the appropriate images 112 to selected display devices 110a-d of the plurality of display devices 110a-110d according to the hanging protocol and the determined relative positions of the display devices.

It will be appreciated that utilisation of hanging protocols in this way can result in easier set up of the combined display. Furthermore, use of features of the display devices 110a-d, such as position determination apparatus 215, in conjunction with the use of hanging protocols, can further facilitate formation of the combined display and preferably also automation of the process of setting up the combined display/shared work session. It will also be appreciated that the joining of display devices 110a-110d into the image display system 105 can be as the result of a user action, such as a "bumping" gesture and/or carried out automatically, wherein it will be appreciated that suitable safeguards such as joining rules, passwords, device authentication and clearance, and/or the like could be used.

Various methods may be used to join display devices to a collaboration to display medical images, including each device consenting to the collaboration, agreeing what patient case to view, selecting what views to display and assigning them to suitable display areas on each device.

Individual user or group preferences may be taken into account when establishing a collaboration. For example, people to include/exclude from a particular collaboration may be identified, or particular protocols may be always used for a particular context/group.

Figure 4:
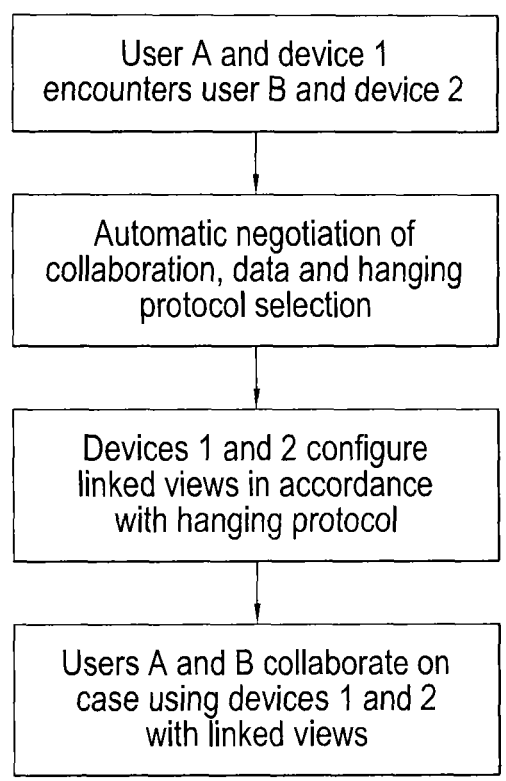
FIG. 4 is a flowchart illustrating a process for connecting the display devices of FIG. 3.

An example of an operation of the image display system 105 according to embodiments of the invention is illustrated in overview in the flowchart of FIG. 4. In this case, a first user (user A) carrying a first display device 110a such as a tablet computer (referred to as device 1) encounters a second user (user B) carrying a second display device 110b such as a smartphone (referred to as device 2). One or both of the first and/or second users indicate that they wish to collaboratively view medical images relating to a given procedure. The first and second display devices 110a, 110b automatically detect the presence of the other device 110a, 110b using position determination apparatus 215 such as near field communications apparatus. Based on data input by one (or all) of the users, data stored in the data storage 205 of the users' device(s) 110a, 110b and data retrieved from networked data storage 120, the layout unit 135 determines an appropriate hanging display for the users, the procedure and devices 110a, 110b. These actions form an automatic negotiation of collaboration, data and hanging protocol selection between the display devices 110a, 110b. Both display devices 110a, 110b reconfigure their displays 220 according to the hanging protocol and appropriate images are provided to the display devices 110a, 110b for display thereon according to the hanging protocol. The users can then collaborate using both the first and second display devices 110a, 110b with linked views governed by the hanging protocol.

Figure 5:
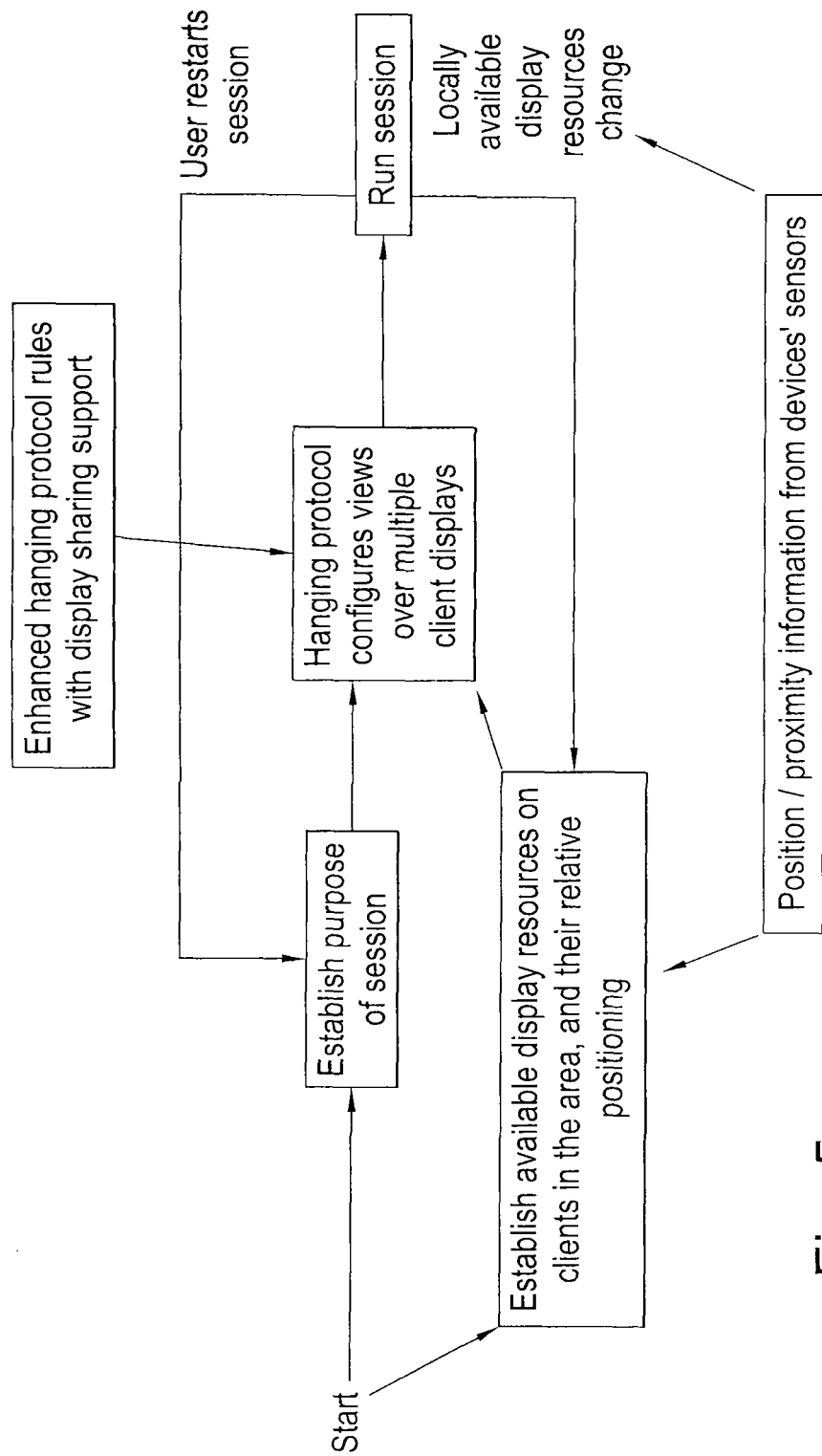
FIG. 5 is a flowchart illustrating an operating method for image display systems according to embodiments of the invention.

A method of providing automated collaboration between display devices 110a, 110b for displaying medical images according to embodiments of the invention is illustrated in overview in the flowchart of FIG. 5. When an image display session is started by a user using their display device 110a, the system 105 establishes the purpose of the session. This can be, for example, via user input, stored data or via use of defaults or the like. The system 105 then automatically detects and identifies available display 220 resources on any display devices 110a, 110b in the vicinity of the user. The system 105 also determines the relative position of the display devices 110a, 110b using the position determination apparatus 215 of the display devices 110a, 110b. This device and position data, along with the data obtained when establishing the purpose of the session, is used by the layout unit 135 to select an appropriate hanging protocol. The allocation unit 140 then configures the views provided on the displays 220 of each of the plurality of display devices 110a, 110b and allocates images 112 to be displayed on each of the display devices 110a, 110b according to the hanging protocol. The images 112 can then be viewed on the plurality of display devices 110a, 110b according to the hanging protocol until a user restarts the session or the locally available display resources change.

Figure 6:
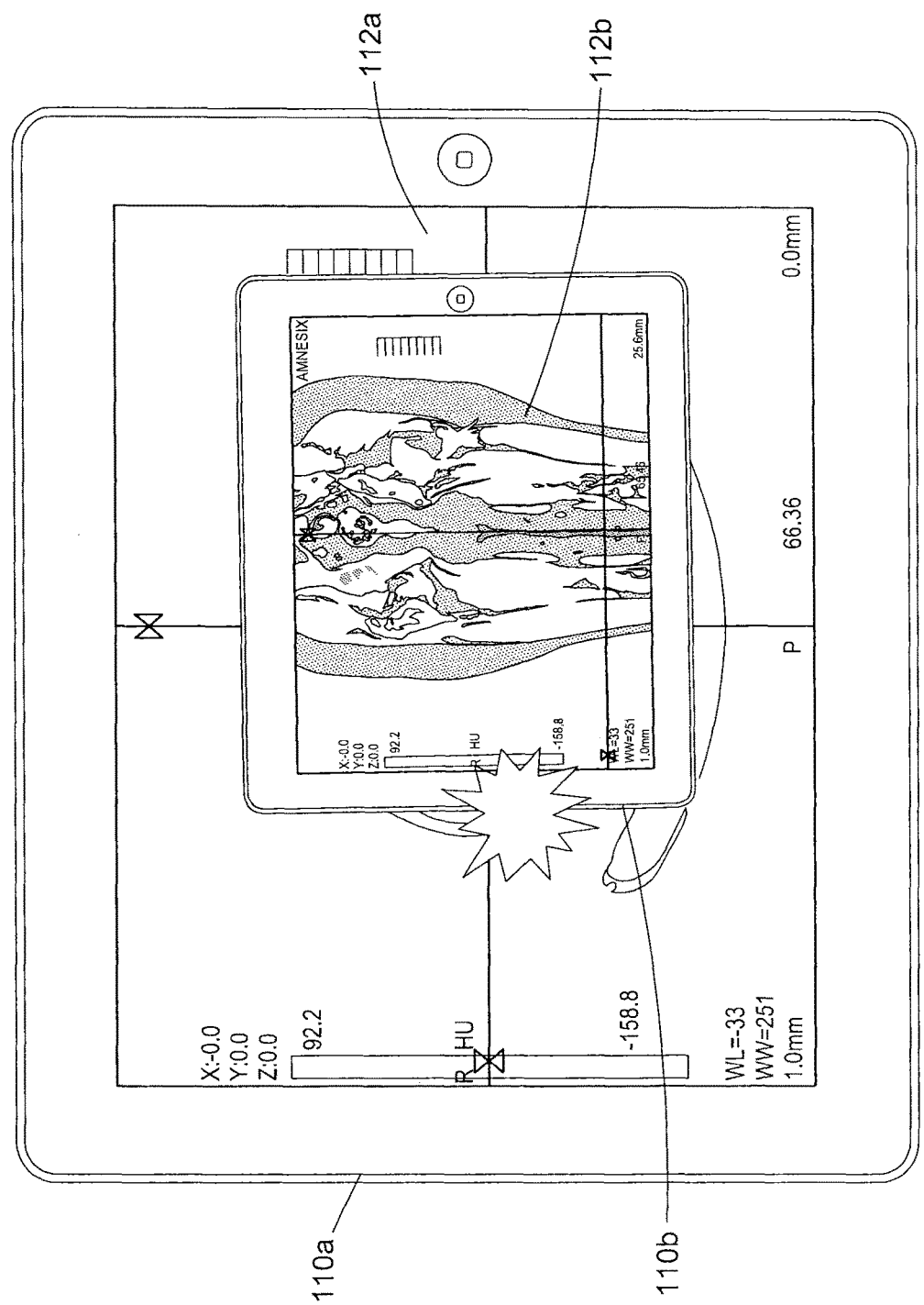
FIG. 6 illustrates the connecting of two component display devices for use in image display systems according to embodiments of the invention.
Figure 7:
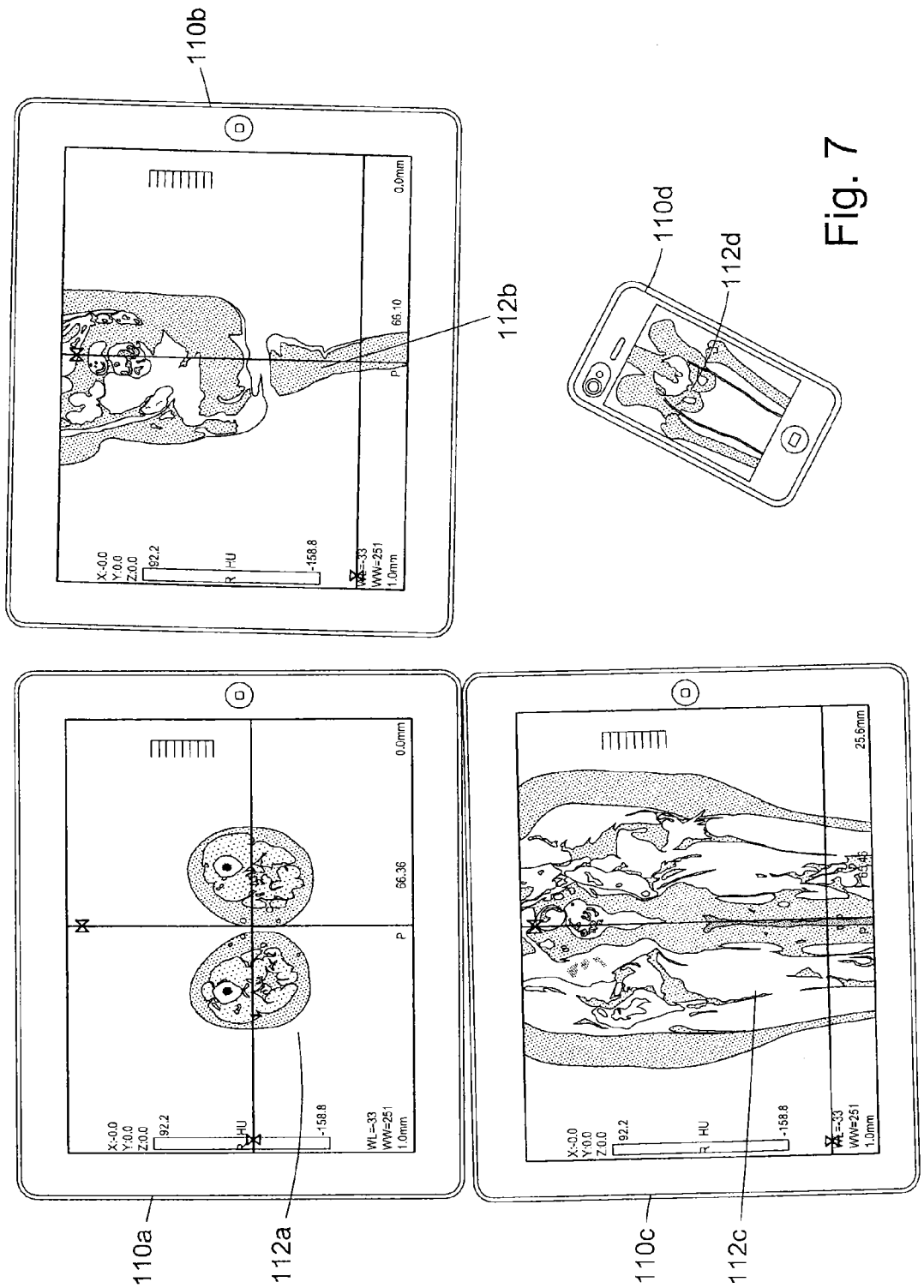
FIG. 7 illustrates a combined display provided by the imaging system according to embodiments of the present invention.

An example of a session initiation is described with reference to FIG. 6. In this case, two display devices 110a, 110b in the form of tablet computers are bumped together or placed in close proximity. The position determination apparatus 215 of the display devices 110a, 110b comprises at least an accelerometer and near field communication apparatus. The accelerometer on each device is used to determine the "bump" together gesture that is indicative of a pairing. Upon identifying this gesture, the two devices can communicate via near field communications. The near field communications apparatus on each device are used to identify the display devices 110a, 110b and provide position and device information, such as model type. Further display devices 110a, 110b such as tablet computers and smart phones can then be bumped together or placed in proximity as required to form the combined image display. For example, rather than display four views (e.g. views through a transverse or axial plane, a coronal plane and a sagittal plane and a 3D volume rendered representation) in a 2×2 tiled arrangement on a single display, the required views are displayed on a 2×2 tiled arrangement formed by four separate display devices 110a, 110b, 110c, 110d, with a different image 112a-d being displayed on each display device 110a, 110b, 110c, 110d, as shown in FIG. 7.

Figure 8:
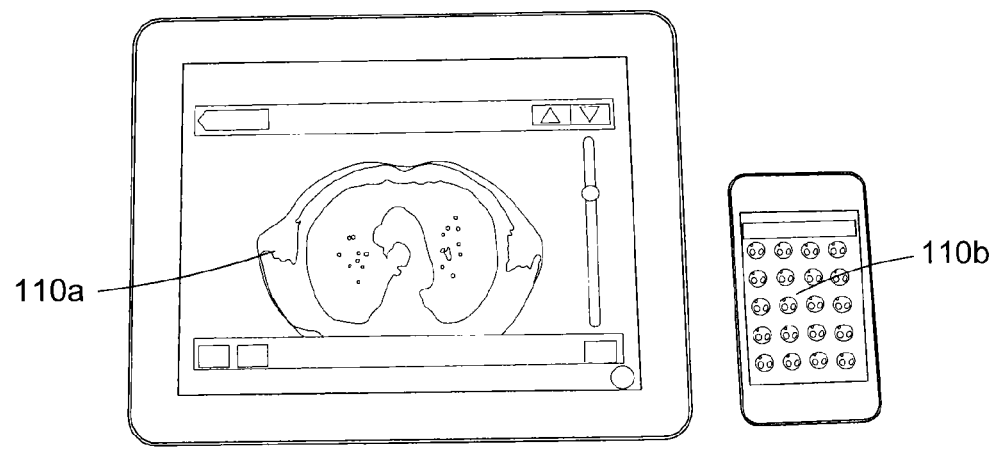
FIG. 8 illustrates an alternative combined display provided by the imaging system of embodiments of the present invention.
Figure 9:
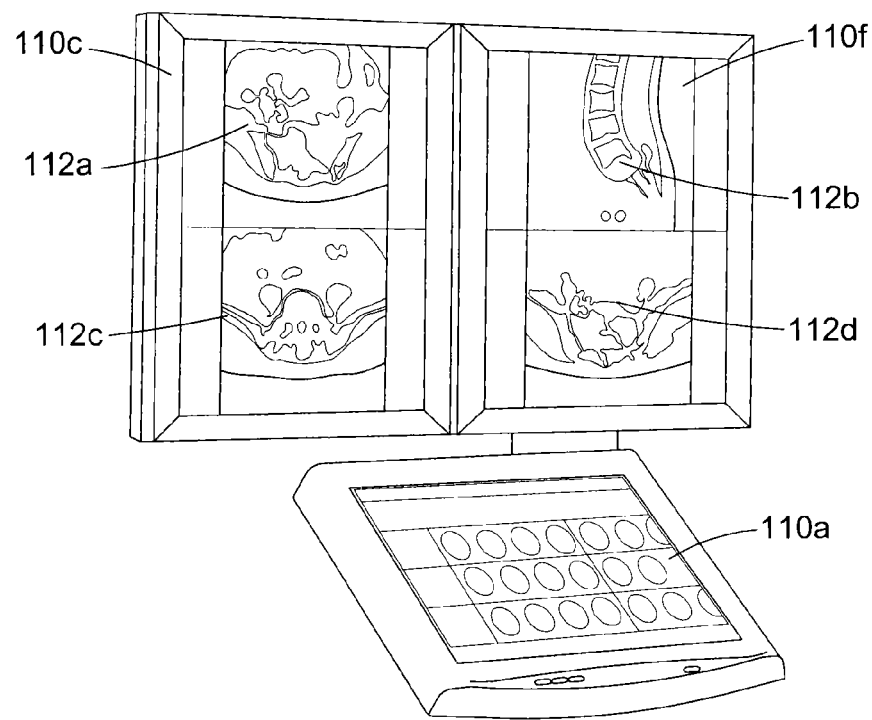
FIG. 9 illustrates another combined display provided by the imaging system according to embodiments of the present invention.

However, it will be appreciated that other arrangements can be used. For example, FIG. 8 shows a display presented on a pair of display devices consisting of a tablet 110a and a phone 110b provided side by side. In this case, the tablet 110a has been recruited to display a larger version of one of the many smaller images that are displayed on the phone 110b. FIG. 9 shows a tablet computer 110a display a plurality of images, and a composite display using two side by side monitors 110e, 110f each recruited to display larger versions of two of the images displayed on the tablet computer 110a so as to form a 2×2 tiled combined display.

As an example of the use of the system 105 according to an embodiment, a cardiologist receives a request to do an emergency read of imaging data via their smartphone 110a. The radiologist can then place their tablet computer 110b adjacent to the smartphone 110a. Upon receiving the request at the smartphone 110a, the smartphone 110a is configured to automatically search for nearby devices. The smartphone 110a detects the presence of the tablet computer 110b through one of the methods described above, such as use of near field communications apparatus, GPS data and/or detection of gestures using sensors and also determines that the tablet computer 110b is cleared for collaborating. Upon determining the presence and relative position of the of the tablet computer 110b, the smart phone 110a can then automatically determine the display properties of the tablet computer 110b and select an appropriate hanging protocol based on the purpose of the session, as indicated in the data received on the smartphone 110a, the capabilities of the devices 110a, 110b and the preferences of the cardiologist. The images 112a, 112b required for the session, as specified in the hanging protocol, can then be retrieved over a network connection and distributed to the smartphone 110*a* and tablet computer 110*b* depending on their relative positions, as specified in the hanging protocol.

In another example, a radiologist A encounters two doctors B and C in a corridor and raises a question about a patient's scan history. The radiologist and both doctors have tablet computers 110*a*, 110*b*, 110*c*. The radiologist and the two doctors place their tablets 110*a*, 110*b*, 110*c* together and the radiologist selects a distributed hanging protocol. The radiologist's tablet 110*a* then searches for nearby devices and automatically recruits the doctor's tablets 110*b*, 110*c* and uses them to view selected images from a single application session using the combined display area of all three tablet computers 110*a*, 110*b*, 110*c*.

In another example, a radiologist visits a patient in a ward bay. The radiologist has a hanging protocol configured in his tablet computer 110*a* that automatically expands his display area to detect and utilize a large screen 110*b* in the ward bay to display images, e.g. flythrough images, to the patient and the students.

Optionally, display devices 110*a-d* can be configured to store and exchange data regarding a user associated with the display device 110*a-d*, such as expertise, position, job title, preferences and the like. In an example of how this could be used, a radiologist meets a surgeon to discuss a case and both are carrying display devices 110*a*, 110*b*, e.g. tablet computers. The radiologist's tablet computer 110*a* detects the presence of the surgeon's tablet computer 110*b*, as described above. Amongst the information shared by the display devices 110*a*, 100*b* is data regarding the user of the display device 110*a*, 110*b*, e.g. an indication of the identity and expertise of the user. In this case since the radiologist's tablet 110*a* can determine that the other display device 110*b* is associated with a surgeon, the radiologist's display device 110*a* selects a hanging protocol that provides a surgical planning oriented layout using both display devices 110*a*, 110*b*. Advantageously, the view(s) of most interest to each user can be displayed on the appropriate display device 110*a*, 110*b*.

Optionally, the automated connection between display devices 110*a*, 110*b* can be customized and/or specified by a user. For example, if two radiologists do not get on or simply do not work together, they can configure their display devices 110*a*, 110*b* to take this into account. In this case, if the two such radiologists are browsing multiplanar reconstructions using their display devices 110*a*, 110*b* in the form of tablet computers, then once the display devices 110*a*, 110*b* discover the identity of the user associated with the other display device 110*a*, 110*b*, they are configured not to attempt to automatically open a common session.

In another example, several radiologists, each having their own display device 110*a-d* in the form of a tablet computer, are attending a case conference. The room in which the case conference is held is equipped with a projector controlled by a personal computer. The personal computer is running a radiology application that works through a case list. The personal computer can apply the methods described above to determine which display device 110*a-d* is associated with which user. The personal computer can then determine the responsible clinician for each case from the case list and open up a shared display session based on a hanging protocol from that user's display device 110*a-d* when their case comes up for review.

In another example, a radiologist has a display device 110*a* in the form of a laptop and is running medical imaging software on it. The radiologist plugs a projector 110*b* into the laptop. The laptop 110*a* is configured to recognise the extra display device 110*b*, update or select a new hanging protocol if required and reconfigures the application views accordingly.

It is a feature of certain of the embodiments that views on each device can be manipulated automatically or by a user or (for example, respond to mouse, keyboard and touch input) just as they can when not collaborating. In some embodiments, the hanging protocol allows a cursor or other pointer to pass between views on separate devices. For example a mouse drag initiated within a view on a laptop may move the cursor into a view on a tablet. In such an example, upon a mouse-button-up action, the cursor may be left on the tablet view, where it can be picked up using the touch-screen interface.

In some embodiments, the hanging protocol or other layout data provides rules such that a corresponding change in the medical image displayed on one of the display devices is generated automatically in response to a change in the medical image displayed on at least one other one of the display devices. The change in the medical image may comprise, for example at least one of a change in rendering, a change in position, orientation or co-ordinates, a change in view point, a change in position of a pointer, at least one of a pan, scale, position or scale adjustment. The hanging protocol may be configured to provide synchronised navigation of the medical images across the plurality of display devices. Views on each device may respond appropriately to changes made on linked views on another device, for example, contrast, pan, position or scale adjustments.

In some embodiments, collaborative hanging protocols, or other layout data, include data representing the relative importance of particular views. For example, a hanging protocol in some embodiments assigns a relative importance to each of the plurality of medical images in some embodiments. The allocation unit may be configured to determine, for at least one of the views, in dependence on the relative importance of that view and the number of the display devices available, whether to display that view. The allocation unit may also be configured to determine in dependence on the relative importance of the views and in dependence at least one property of the display devices, at least one of the position, scale or resolution or display device assigned to each image. Thus, for example, according to the number and size/resolution of displays available, the allocation unit may be configured to choose whether to include a particular view, at what scale to display each included view, and on which display or area of a display to locate each included view.

In addition to display of images, some collaborative protocols may include lists (for example of patients, studies, findings etc.) or graphical content (for example, lab results or other analysis results).

Multi-device, multi-role hanging protocols can be defined (either by software designer or by users) that are based on existing hanging protocols for each role but that take into account the clinical/geometrical/etc. interrelationships between those role-based protocols. For example, if a surgeon typically works from a set of selected key images (of various types e.g. planar, MPR, volume rendered) rather than from the original scan data, then the collaborative protocol may be capable of displaying each of these key images in the surgeon's view while simultaneously automatically scrolling original or MPR images to an equivalent location/viewpoint within a radiologist's view.

Similarly, an oncologist may be considering a set of key images previously identified by the radiologist as showing cancerous nodules. Displaying each of these findings in the oncologist's views may cause the radiologist's views to navigate to the equivalent position in the original images.

In certain embodiments, the allocation unit is configured to allocate the plurality of medical images amongst the plurality of display devices subject to the plurality of display devices subscribing to a collaboration, and the allocation unit is further configured to at least one of reassign the images or alter at least one display parameter in response to one of the plurality of display devices leaving the collaboration.

In embodiments hanging protocols or other layout data comprising rules concerning allocation of images to a display device, may be used to determine the layout of any suitable type of medical images. The medical images may comprise but are not limited to, for example, a plurality of views of the same anatomical region of a patient, a plurality of views obtained using different imaging modalities (for example, CT, X-ray, MRI or PET imaging) a plurality of different views obtained by differently rendering the same volumetric image data.

Embodiments may provide hanging protocols that suit the capability of PACS viewers or other software-based viewers, taking account of additional criteria such as, for example, number, resolution, type and relative position of available monitors, linkage of user- and automatically-controlled actions such as scroll, contrast adjustment and others, information about the clinicians, patient, study or other properties for example encoded in the meta-data associated with the loaded images.

Some embodiments may implement certain functionality by means of a computer program having computer-readable instructions that are executable to perform the method of the embodiments. The computer program functionality could be implemented in hardware (for example by means of a CPU or by one or more ASICs (application specific integrated circuits)), FPGAs (field programmable gate arrays) or GPUs (graphic processing units) or by a mix of hardware and software.

Specific examples of display devices 110a-d such as tablet computers, laptops and smartphones have been described in relation to specific embodiments and examples. However, the display devices 110a-d are not limited to these specific display devices but instead any suitable device having a display and communications ability could be used instead.

Furthermore, although various specific examples of position determination apparatus 215 have been described, such as GPS sensors, near field communications apparatus, short range communications apparatus such as Bluetooth and IR communications apparatus, cameras, accelerometers and user input apparatus has been described, it will be appreciated that other suitable apparatus capable of determining the presence and/or identity and/or position and/or relative position of a display device 110 could be used.

In addition, although certain features have been described in relation to servers and/or networked storage or other devices, and certain features have been described in relation to display devices 110a-d, it will be appreciated that one or more feature described in relation to a server, networked storage or other networked function may be provided in a display device 110a-d.

Furthermore, although certain embodiments of the present invention are described in relation to a server, it will be appreciated that the server need not be a single machine but could comprise a plurality of server units, such as a distributed array.

In addition, although embodiments described above are described in relation to a server system, it will be appreciated that, according to embodiments of the invention, the functions performed by the processing device 125 can comprise or be comprised in or be implemented by the processing device 225 of a display device 110a-d. In this case, position and/or relative position data associated with the plurality of display devices 110a-d can be determined by the display device 110a-d and/or provided to the display device 110a-d by other display devices 110a-d. In such systems, one of the display devices 110a-d could simply operate as a server, with processing apparatus that performs both the functions described in relation to the processing apparatus 125 of the image display system 105 and the processing apparatus 225 of the display devices 110a-d. However, it will be appreciated that one or more of the functions described in relation to the image processing apparatus 105 may be provided or distributed in or performed by two or more of the display devices 110a-d.

For example, in some embodiments one or more of the display devices 110a-d acts as a thin client and relies on image processing and rendering to take place largely on a server. Display images are transmitted by wire or wireless. User inputs made at the device are communicated to the server, and their implications for all collaborating devices interpreted and acted upon at the server.

In some embodiments, one or more of the display devices 110a-d loads or stores image data locally and perform image processing and rendering locally, producing its own images for display. It may communicate its user inputs and other status to a server, which interprets and acts upon any implications for all collaborating display devices.

In some embodiments, one or more of the display devices 110a-d act as server for at least some of the other collaborating display devices, performing appropriate image processing and rendering on their behalf, and transmitting images to those other display devices, for example via a network and/or using peer-to-peer distribution.

Furthermore, although embodiments have been described that utilise automated connection of display devices 110a-d, it will be appreciated that connection of display devices 110a-d need not be automated and may instead be partially or fully manual.

Furthermore, although the above invention has been described in relation to the display of images, it will be appreciated that data or other items of interest could be displayed in place of one of more of the images.

Whilst particular units have been described herein, in alternative embodiments functionality of one or more of those units can be provided by a single unit, processing resource or other component, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A display system for collaboratively displaying a plurality of separate medical images across a plurality of separate display devices, the system comprising:
processing circuitry connected to the plurality of separate display devices and configured to
provide a hanging protocol specifying the plurality of separate medical images to be displayed and a relative position in which each of the separate medical images is to be displayed;
obtain, from each of the plurality of separate display devices, consent to join a collaboration with other of the plurality of separate display devices, in order to display the plurality of separate medical images across the plurality of separate display devices, wherein establishment of the collaboration is dependent on at least one of user preference, group preference, a person using at least one of the separate display devices, and particular protocols used;
automatically assign each of the plurality of separate medical images to one of the plurality of separate display devices according to the hanging protocol; and
in response to receiving the consent to join the collaboration from each of the plurality of separate display devices, display the plurality of separate medical images concurrently on the plurality of separate display devices to obtain a collaborative display of the medical images across the plurality of separate display devices,
wherein at least one of the plurality of separate display devices comprises a mobile display device, and
the processing circuitry is further configured to
automatically detect a physical location of each of the plurality of separate display devices,
select, based on the detected physical location of each of the separate display devices, at least one device out of the detected plurality of separate display devices, and
after receiving the consent from the selected at least one device, assign at least one of the plurality of separate medical images for display on the selected at least one device, based on the hanging protocol and at least one of the detected location and an orientation of the selected at least one device with respect to the mobile display device.

2. The display system according to claim 1, wherein the processing circuitry is configured to provide the hanging protocol, which comprises a plurality of rules concerning at least one of allocation to a display device, image appearance, image orientation, image data selection, image rendering, image importance, and image navigation.

3. The display system according to claim 1, wherein the processing circuitry is configured to provide the hanging protocol, which is a DICOM-compliant hanging protocol.

4. The display system according to claim 1, wherein processing circuitry is further configured to obtain the plurality of separate medical images, which comprise at least one of:
a plurality of views of the same anatomical region of a patient;
a plurality of views obtained using different imaging modalities; and
a plurality of different views obtained by differently rendering a same volumetric image data.

5. The display system according to claim 1, wherein the display system comprises at least one position determination sensor configured to detect the physical location of each of the plurality of separate display devices.

6. The display system according to claim 1, wherein the processing circuitry is further configured to allocate the plurality of medical images to the display devices according to the hanging protocol and the physical locations of the display devices.

7. The display system according to claim 1, wherein in selecting the at least one device out of the detected plurality of separate display devices, the processing circuitry is further configured to select those previously-detected display devices that are separated by less than a threshold distance from each other.

8. The display system according to claim 1, further comprising a user input device, wherein the processing circuitry is further configured to output a list of available display devices, to receive user input via the user input device selecting a plurality of the available display devices, and to assign the plurality of medical images to the selected display devices according to the hanging protocol.

9. The display system according to claim 8, wherein the list of available display devices is a list of further display devices that are within a threshold distance of a first display device.

10. The display system according to claim 1, wherein the processing circuitry is further configured to generate automatically a corresponding change in a medical image displayed on one of the display devices in response to a change in a medical image displayed on at least one other one of the display devices.

11. The display system according to claim 10, wherein the processing circuitry is configured to generate the change in the medical image, which comprises at least one of a change in rendering, a change in position, orientation or co-ordinates, a change in view point, a change in position of a pointer, and at least one of a pan, scale, position and scale adjustment.

12. The display system according to claim 1, wherein the processing circuitry is further configured to provide synchronized navigation of the medical images across the plurality of display devices.

13. The display system according to claim 1, wherein the processing circuitry is configured to provide the hanging protocol, which assigns a relative importance to each of the plurality of medical images.

14. The display system according to claim 13, wherein the processing circuitry is further configured to determine, for at least one medical image of the medical images, in dependence on the relative importance of the one medical image and a number of the display devices available, whether to display the one medical image.

15. The display system according to claim 13, wherein the processing circuitry is further configured to determine, in dependence on the relative importance of the medical images and in dependence on at least one property of the display devices, at least one of position, scale, and resolution of the display device assigned to each medical image.

16. The display system according to claim 1, wherein at least one display device of the plurality of display devices comprises a sensor configured to determine the orientation of the display device and to update an orientation of the medical image displayed on that display device automatically in response to a change in orientation of the display device.

17. The display system according to claim 1, wherein the processing circuitry is further configured to assign the plurality of medical images to the plurality of display devices subject to the plurality of display devices subscribing to a collaboration, and the circuitry is further configured to at least one of reassign the images and alter at least one display parameter in response to one of the plurality of display devices leaving the collaboration.

18. The display system according to claim 1, further comprising a server that includes the processing circuitry, and that further includes a circuit configured to render the medical images and distribute the rendered medical images to at least some of the plurality of display devices.

19. The display system according to claim 1, wherein at least one of the display devices comprises the processing circuitry, and is configured to control the assignment of the images to the other display devices.

20. The display system according to claim 1, further comprising a device discovery circuit configured to discover display devices in a vicinity of the display system.

21. The display system according to claim 19, wherein the device discovery circuit is configured to discover display devices using at least one of Global Positioning System (GPS), near field or short range wireless communication apparatus, a Bluetooth, ZigBee or Infrared (IR) communication apparatus, a camera, and an accelerometer.

22. The system according to claim 1, wherein the processing circuitry is further configured to dynamically modify or replace a layout of the medical images in response to at least one of changes in display devices available to the system and user input.

23. The system according to claim 1, wherein the processing circuitry is further configured to assign at least one medical image to a display device having a location relative to the other display device that best matches the relative image position specified in the hanging protocol for the assigned medical image.

24. The system according to claim 1, wherein the processing circuitry is further configured to select the hanging protocol according to at least one of a user's expertise, a user's job title, a user's interest in a field, user preferences, a display resolution or other display property of at least one of the display devices, a display size of at least one of the display devices, whether a display device is a color or grayscale display device, whether a display device has an electronic ink display, a modality associated with the images, a procedure associated with the images, and anatomy associated with the images.

25. The system according to claim 1, wherein the processing circuitry is further configured to select or change the hanging protocol based on usable system resources, including at least one of CPU usage and memory usage.

26. A mobile display device for collaboratively displaying a plurality of separate medical images in collaboration with at least one other display device, the mobile display device comprising:
a display;
a communication circuit configured to communicate with the at least one other display device;
processing circuitry connected to the at least one other display device and configured to
provide a hanging protocol specifying the plurality of separate medical images to be displayed and a relative position in which each of the separate medical images is to be displayed;
obtain, from each of the at least one other display device, consent to join a collaboration with the mobile display device and other of the at least one other display device, in order to display the plurality of separate medical images across the at least one other display device and the display, wherein establishment of the collaboration is dependent on at least one of user preference, group preference, a person using the at least one of the at least one other display device, and particular protocols used;
automatically assign each of the plurality of separate medical images to one of the mobile display device and at least one other display device according to the hanging protocol; and
in response to receiving the consent to join the collaboration from each of the at least one other display device, cause the display to display the plurality of separate medical images concurrently on the display and the at least one other display device to obtain a collaborative display of the medical images across the at least one other display device and the display,
wherein the processing circuitry is further configured to
automatically detect a physical location of each of the at least one other display device,
select, based on the detected physical location of each of the separate display devices, a device from among the detected at least one other display device, and
after receiving the consent from the selected device, assign at least one of the plurality of separate medical images for display on the selected device, based on the hanging protocol and at least one of the detected physical location and an orientation of the selected device with respect to the mobile display device.

27. The mobile display device according to claim 26, wherein the mobile display device comprises at least one position determination sensor configured to detect the physical location of the mobile display device and the at least one other display device, and the processing circuitry is further configured to assign each of the plurality of separate medical images to one of the mobile display device and the at least one other display device according to the hanging protocol and the physical locations of the display devices.

28. A server for processing a plurality of separate medical images, the server comprising:
processing circuitry configured to
provide a hanging protocol specifying the plurality of separate medical images to be displayed and a relative position in which each of the separate medical images is to be displayed;
obtain, from each of a plurality of separate display devices, consent to join a collaboration with other of the plurality of separate display devices, in order to display the plurality of separate medical images across the plurality of separate display devices, wherein establishment of the collaboration is dependent on at least one of user preference, group preference, a person using at least one of the separate display devices, and particular protocols used;
automatically assign each of the plurality of separate medical images to one of the plurality of separate display devices according to the hanging protocol; and
in response to receiving the consent to join the collaboration from each of the plurality of separate display devices, display the plurality of separate medical images concurrently on the plurality of separate display devices to obtain a collaborative display of the medical images across the plurality of separate display devices, wherein at least one of the plurality of display devices comprises a mobile display device, and the processing circuitry is further configured to automatically detect a physical location of each of the plurality of separate display devices, select, based on the detected physical location of each of the separate display devices, at least one device out of the detected plurality of separate display devices, and after receiving the consent from the selected at least one device, assign at least one of the plurality of separate medical images for display on the selected at least one device, based on the hanging protocol and at least one of the detected physical location and an orientation of the selected at least one device with respect to the mobile display device.

29. The server according to claim 28, wherein the server comprises at least one position determination sensor configured to detect the physical location of each of the plurality of display devices; and the processing circuitry is further configured to assign each of the plurality of separate medical images to one of the plurality of display devices according to the hanging protocol and the detected physical locations of the display devices.

30. A method for collaboratively displaying a plurality of separate medical images across a plurality of separate display devices, the method comprising:

providing a hanging protocol specifying the plurality of medical images to be displayed and a relative position in which each of the separate medical images is to be displayed;

obtain, from each of the plurality of separate display devices, consent to join a collaboration with other of the plurality of separate display devices, in order to display the plurality of separate medical images across the plurality of separate display devices, wherein establishment of the collaboration is dependent on at least one of user preference group preference, a person using at least one of the separate display devices, and particular protocols used;

automatically assigning each of the plurality of separate medical images to one of the plurality of separate display devices according to the hanging protocol, in response to receiving the consent to join the collaboration from each of the plurality of separate display devices, displaying the plurality of separate medical images concurrently on the plurality of separate display devices to obtain a collaborative display of the medical images across the plurality of separate display devices, wherein at least one of the plurality of display devices comprises a mobile display device, and the method further includes automatically detecting a physical location of each of the plurality of separate display devices, selecting, based on the detected physical location of each of the separate display devices, at least one device out of the detected plurality of separate display devices, and after receiving the consent from the selected at least one device, assigning at least one of the plurality of separate medical images for display on the selected at least one device, based on the hanging protocol and at least one of the detected physical location and an orientation of the selected at least one device with respect to the mobile display device.

31. The method according to claim 30, further comprising detecting a physical location of each the plurality of display devices, wherein assigning the plurality of separate medical images comprises assigning the plurality of separate medical images to the display devices according to the hanging protocol and the detected physical locations of the display devices.

32. A display system for collaboratively displaying a plurality of separate medical images across a plurality of separate display devices, the system comprising:

processing circuitry connected to the plurality of separate display devices and configured to provide a hanging protocol specifying the plurality of medical images to be displayed and a relative position in which each of the separate medical images is to be displayed;

obtain, from each of the plurality of separate display devices, consent to join a collaboration with other of the plurality of separate display devices, in order to display the plurality of separate medical images across the plurality of separate display devices, wherein establishment of the collaboration is dependent on at least one of user preference, group preference, a person using at least one of the separate display devices, and particular protocols used;

automatically assign each of the plurality of separate medical images to one of the plurality of separate display devices according to the hanging protocol; and in response to receiving the consent to join the collaboration from each of the plurality of separate display devices, display the plurality of separate medical images concurrently on the plurality of separate display devices to obtain a collaborative display of the medical images across the plurality of separate display devices, wherein at least one of the plurality of separate display devices comprises a mobile display device, and the processing circuitry is further configured to automatically detect a physical location of each of the plurality of separate display devices, select, based on the detected physical location of each of the separate display devices, at least one device out of the detected plurality of separate display devices, and after receiving the consent from the selected at least one device, assign at least one of the plurality of separate medical images for display on the selected at least one device, based on the hanging protocol and at least one of the detected physical location and an orientation of the selected at least one device with respect to the mobile display device.

* * * * *